(12) United States Patent
Wang et al.

(10) Patent No.: US 12,383,341 B2
(45) Date of Patent: Aug. 12, 2025

(54) SYSTEMS AND METHODS FOR AUTOMATICALLY GENERATING AN ANATOMICAL BOUNDARY

(71) Applicant: INTUITIVE SURGICAL OPERATIONS, INC., Sunnyvale, CA (US)

(72) Inventors: Bai Wang, Palo Alto, CA (US); Energy Cruse, II, Foster City, CA (US); Joy Janku, San Francisco, CA (US); Sida Li, San Jose, CA (US); Hui Zhang, San Jose, CA (US); Tao Zhao, Sunnyvale, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 344 days.

(21) Appl. No.: 17/789,958

(22) PCT Filed: Dec. 19, 2020

(86) PCT No.: PCT/US2020/066268
§ 371 (c)(1),
(2) Date: Jun. 29, 2022

(87) PCT Pub. No.: WO2021/138097
PCT Pub. Date: Jul. 8, 2021

(65) Prior Publication Data
US 2023/0034112 A1 Feb. 2, 2023

Related U.S. Application Data

(60) Provisional application No. 62/955,181, filed on Dec. 30, 2019.

(51) Int. Cl.
*A61B 34/20* (2016.01)
*A61B 34/00* (2016.01)
*A61B 34/10* (2016.01)

(52) U.S. Cl.
CPC .............. *A61B 34/20* (2016.02); *A61B 34/25* (2016.02); *A61B 2034/107* (2016.02)

(58) Field of Classification Search
CPC ... A61B 2034/107; A61B 34/20; A61B 34/25; G06T 2210/41; G06T 2210/21
See application file for complete search history.

(56) References Cited

U.S. PATENT DOCUMENTS 9,439,622 B2 9/2016 Case et al.
10,123,841 B2 * 11/2018 Kim ....................... A61B 34/37
(Continued)

FOREIGN PATENT DOCUMENTS

WO WO-2015099427 A1 7/2015
WO WO-2019048269 A1 * 3/2019

OTHER PUBLICATIONS

International Preliminary Report on Patentability for Application No. PCT/US2020/066268, mailed on Jul. 14, 2022, 7 pages.
(Continued)

*Primary Examiner* — Jeffrey G Hoekstra
*Assistant Examiner* — Nyrobi Celestine
(74) *Attorney, Agent, or Firm* — Haynes & Boone, LLP

(57) ABSTRACT

A medical system comprises a display system, a user input device, and a control system communicatively coupled to the display system and the user input device. The control system is configured to display image data of an anatomical region via the display system, determine a target location in the anatomical region, and determine an anatomical boundary based on the target location. The anatomical boundary indicates a surface of an anatomical structure in the ana-
(Continued)

tomical region. The control system is further configured to determine a trajectory zone around a path between an exit point and the target location. The control system is further configured to determine a zone boundary based on an intersection of the trajectory zone with the anatomical boundary.

20 Claims, 11 Drawing Sheets

(56) References Cited

U.S. PATENT DOCUMENTS

| | | | | |
|---|---|---|---|---|
| 2009/0149867 A1* | 6/2009 | Glozman | ............... | A61B 34/70 600/407 |
| 2011/0306985 A1* | 12/2011 | Inoue | .................... | A61B 34/30 606/130 |
| 2014/0303486 A1* | 10/2014 | Baumgartner | ......... | A61B 5/055 600/414 |
| 2015/0148690 A1* | 5/2015 | Chopra | ................ | A61B 5/6852 600/478 |
| 2016/0106957 A1* | 4/2016 | Olson | ................... | A61B 34/71 604/95.04 |
| 2018/0021097 A1 | 1/2018 | Quaid et al. | | |
| 2018/0055575 A1* | 3/2018 | Krimsky | ................ | A61B 90/37 |
| 2018/0060524 A1* | 3/2018 | Krimsky | ................ | G16H 50/30 |
| 2018/0217734 A1* | 8/2018 | Koenig | ................ | A61B 34/25 |
| 2018/0333207 A1* | 11/2018 | Moctezuma De la Barrera | .......... | A61B 34/30 |
| 2019/0008591 A1* | 1/2019 | Desai | .................... | G06T 7/0012 |
| 2019/0159844 A1* | 5/2019 | Daniels | .................. | A61B 5/055 |
| 2019/0247122 A1* | 8/2019 | D'Amelio | ............. | A61B 34/10 |
| 2019/0247130 A1* | 8/2019 | State | ...................... | A61B 34/20 |
| 2020/0054399 A1* | 2/2020 | Duindam | ............... | A61B 34/37 |
| 2020/0188025 A1* | 6/2020 | Becker | .................. | A61B 34/30 |
| 2020/0205902 A1* | 7/2020 | Hufford | ................ | A61B 1/018 |
| 2020/0297433 A1* | 9/2020 | Meagher | ................. | G06T 7/40 |
| 2022/0071703 A1* | 3/2022 | Bharadwaj | ............ | G16H 20/40 |
| 2022/0338945 A1* | 10/2022 | Kim | ...................... | A61B 34/10 |
| 2022/0409282 A1* | 12/2022 | Shochat | ................ | A61B 34/32 |

OTHER PUBLICATIONS

International Search Report and Written Opinion for Application No. PCT/US2020/066268, mailed Mar. 31, 2021, 12 pages.

Vertut, J, and Coiffet, P., "Robot Technology: Teleoperation and Robotics Evolution and Development," English translation, Prentice-Hall, Inc., Inglewood Cliffs, NJ, USA 1986, vol. 3A, 332 pages.

* cited by examiner

SYSTEMS AND METHODS FOR AUTOMATICALLY GENERATING AN ANATOMICAL BOUNDARY

CROSS-REFERENCE TO RELATED APPLICATIONS

This application is the U.S. National Phase of International Application No. PCT/US2020/066268, filed Dec. 19, 2020, which designated the U.S. and claims the benefit of and priority to U.S. Provisional Application No. 62/955,181, filed Dec. 30, 2019, and entitled "Systems and Methods for Automatically Generating an Anatomical Boundary," each of which is hereby incorporated by reference herein in its entirety.

TECHNICAL FIELD

The present disclosure is directed to systems and methods for planning and performing an image-guided procedure and more particularly to systems and methods for automatically generating an anatomical boundary that may be viewed and/or manipulated via a graphical user interface.

BACKGROUND

Minimally invasive medical techniques are intended to reduce the amount of tissue that is damaged during medical procedures, thereby reducing patient recovery time, discomfort, and harmful side effects. Such minimally invasive techniques may be performed through natural orifices in a patient anatomy or through one or more surgical incisions. Through these natural orifices or incisions clinicians may insert minimally invasive medical instruments (including surgical, diagnostic, therapeutic, or biopsy instruments) to reach a target tissue location. Some minimally invasive techniques use medical instruments that may be inserted into anatomic passageways and navigated toward a region of interest within the patient anatomy. Control of such an instrument during an image-guided procedure may involve the management of several degrees of freedom of movement including insertion and retraction of the elongate device as well as steering of the device. Improved systems and methods may be used to reduce the risk of patient injury by identifying boundaries when planning the navigation and deployment of the instrument.

SUMMARY

Consistent with some embodiments, a medical system is provided. The system includes a display system, a user input device, and a medical instrument. The system further includes a control system communicatively coupled to the display system and the user input device. The control system is configured to display image data of an anatomical region via the display system and determine a target location in the anatomical region. The control system is further configured to determine an anatomical boundary based on the target location; the anatomical boundary indicates a surface of an anatomical structure in the anatomical region. The control system is further configured to determine a trajectory zone around a path between the medical instrument and the target location. The control system is further configured to determine a zone boundary based on an intersection of the trajectory zone with the anatomical boundary.

In another example, a method of planning a medical procedure is provided. The method includes displaying image data of an anatomical region via a display system and determining a target location in the anatomical region. The method further includes determining an anatomical boundary based on the target location; the anatomical boundary indicates a surface of an anatomical structure in the anatomical region. The method further includes determining a trajectory zone around a path between a medical instrument and the target location. The method further includes determining a zone boundary based on an intersection of the trajectory zone with the anatomical boundary.

In another example, a non-transitory machine readable medium is provided. The non-transitory machine readable medium includes a plurality of machine readable instructions which when executed by one or more processors associated with a planning workstation are adapted to cause the one or more processors to perform a method. The method includes displaying image data of an anatomical region via a display system and determining a target location in the anatomical region. The method further includes determining an anatomical boundary based on the target location; the anatomical boundary indicates a surface of an anatomical structure in the anatomical region. The method further includes determining a trajectory zone around a path between a medical instrument and the target location. The method further includes determining a zone boundary based on an intersection of the trajectory zone with the anatomical boundary.

It is to be understood that both the foregoing general description and the following detailed description are illustrative and explanatory in nature and are intended to provide an understanding of the present disclosure without limiting the scope of the present disclosure. Additional aspects, features, and advantages of the present disclosure will be apparent to one skilled in the art from the following detailed description.

BRIEF DESCRIPTIONS OF THE DRAWINGS

Figure 1:
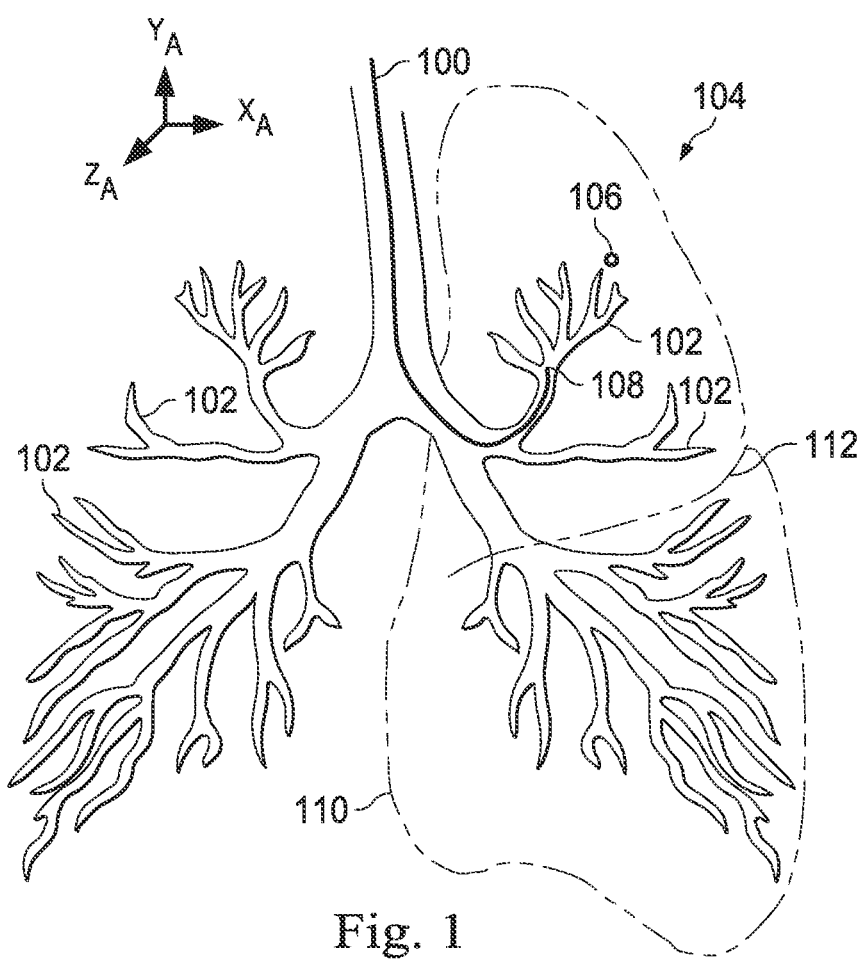
FIG. 1 is a simplified diagram of a patient anatomy according to some examples.

Examples of the present disclosure and their advantages are best understood by referring to the detailed description that follows. It should be appreciated that like reference numerals are used to identify like elements illustrated in one or more of the figures, wherein showings therein are for purposes of illustrating examples of the present disclosure and not for purposes of limiting the same.

DETAILED DESCRIPTION

During the planning and execution of a medical procedure using a steerable medical instrument, an anatomical boundary or a virtual "hazard fence" may be defined by identifying an anatomical surface to be avoided by the medical instrument during the medical procedure. The anatomical boundary may shield vulnerable portions of the anatomy that are in the vicinity of a target location or may protect other anatomical structures of interest from being inadvertently penetrated by the medical instrument. Structures of interest, including vulnerable anatomic structures or surfaces, may include, for example, pulmonary pleurae, pulmonary fissures, large bullae, and blood vessels. For example, puncturing the lung pleura during the medical procedure could cause dangerous pneumothorax to the patient. Generating an anatomical boundary corresponding to the lung pleura would allow the operator to constrain the path of the medical instrument to avoid the vulnerable portion of the anatomy. A candidate path identified during a planning procedure may be identified as invalid when it passes within a threshold distance of a vulnerable portion of the anatomy or breaches a vulnerable portion of the anatomy. Illustrative examples of a graphical user interface for planning a medical procedure, including but not limited to the lung biopsy procedures, are provided below. The graphical user interface may include a plurality of modes including a data selection mode, a hybrid segmentation and planning mode, a preview mode, a save mode, a management mode, and a review mode. Some aspects of the graphical user interface are similar to features described in U.S. Provisional Patent Application No. 62/357,217, titled "Graphical User Interface for Displaying Guidance Information During and Image-Guided Procedure" and filed Jun. 30, 2016, and U.S. Provisional Patent Application No. 62/357,258, titled "Graphical User Interface for Displaying Guidance Information in a Plurality of Modes During Image-Guided Procedure" and filed Jun. 30, 2016, which are incorporated by reference herein in their entirety.

FIG. 1. illustrates an elongated medical instrument 100 extending within branched anatomic passageways 102 of an anatomical region 104 such as human lungs. The anatomical region 104 has an anatomical frame of reference ($X_A$, $Y_A$, $Z_A$). A distal end 108 of the medical instrument 100 may be advanced through the anatomic passageways 102 to perform a medical procedure, such as a biopsy procedure, at or near a target 106. The anatomical region 104 may also include vulnerable surfaces or surfaces that are otherwise of interest when performing the medical procedure. For example, pulmonary pleurae 110 and pulmonary fissures 112 may be surfaces of interest because damaging these surfaces during the medical procedure may injure the patient. Before the medical procedure is performed, pre-operative planning steps may be conducted to plan the medical procedure. In some embodiments, a robot-assisted medical system may be used to plan and execute the medical procedure.

Figure 2A:
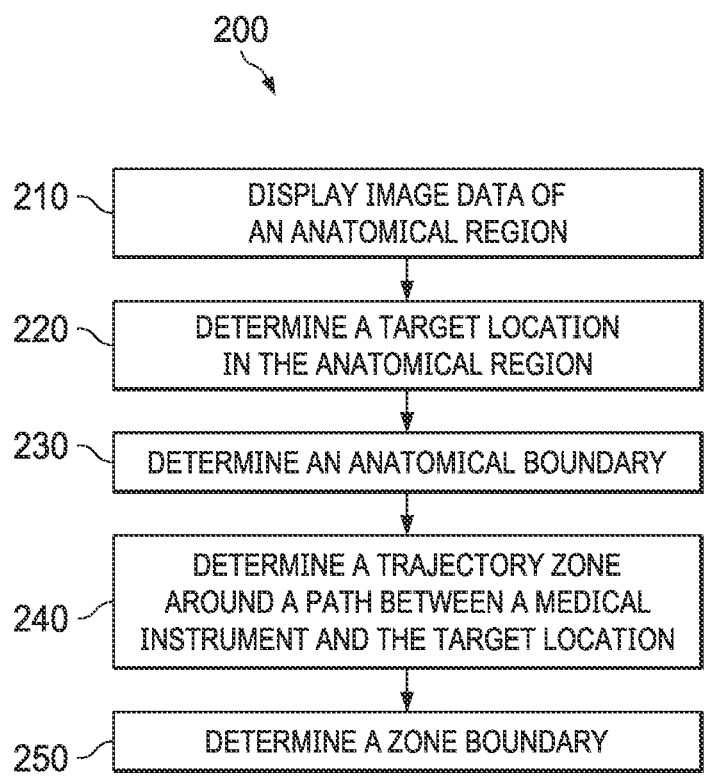
FIG. 2A is a flowchart illustrating a method for generating an anatomical boundary according to some examples.

FIG. 2A illustrates a method 200 for generating an anatomical boundary during the planning of a medical procedure according to some examples. For example, planning a medical procedure may generally include planning trajectories between an initial tool location and one or more anatomical targets. One or more of the method steps may be performed on the same robotic-assisted medical system used to perform a biopsy or other medical procedure. Alternately or additionally, planning may be performed on a different system, such as a workstation dedicated to pre-operative planning. The plan for the medical procedure may be saved (e.g., as one or more digital files) and transferred to the robotic-assisted medical system used to perform the biopsy procedure. The saved plan may include the 3D model, identification of airways, target locations, trajectories to target locations, routes through the 3D model, and/or the like.

Figure 3:
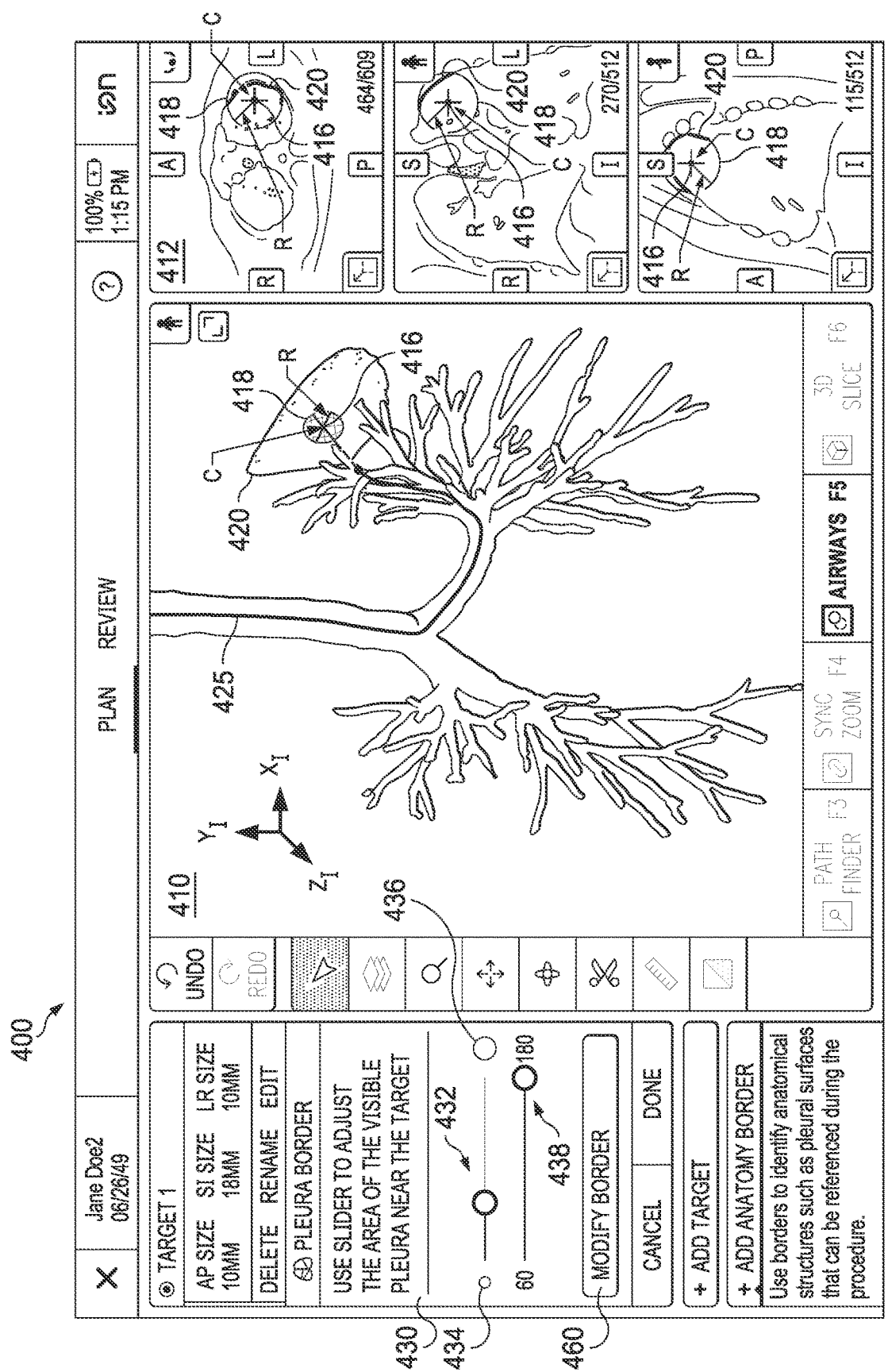
FIG. 3 is a simplified diagram of a graphical user interface during the performance of a method for generating an anatomical boundary according to some examples.

The method 200 is illustrated as a set of operations or processes 210 through 250 and is described with continuing reference to FIG. 3, which illustrates a graphical user interface 400 in a planning mode during the performance of method 200 according to some examples. As shown in FIG. 3, in the planning mode, a traversal path 425 for a medical instrument (e.g., instrument 100) may be planned through an anatomical region (e.g., anatomical region 104) between the mouth of the patient (or any other insertion location where the medical instrument is inserted into the patient) and a target location 416 (e.g., a location of target 106). The traversal path 425 may be generated by a user, a teleoperational control system, or a combination of manual and automatic inputs.

At a process 210, image data of an anatomical region is displayed. For example, as illustrated in FIG. 3, image data 410 corresponding to the three-dimensional anatomical region 104 of a patient is displayed via graphical user interface 400. The displayed image data 410 has an image frame of reference ($X_I$, $Y_I$, $Z_I$). The image data 410 may include, for example, computed tomography (CT) image data. In various alternative examples, image data may be generated using other imaging technologies such as magnetic resonance imaging (MRI), fluoroscopy, thermography, ultrasound, optical coherence tomography (OCT), thermal imaging, impedance imaging, laser imaging, nanotube X-ray imaging, and/or the like. The image data 410 may include multiple images of the three-dimensional anatomical region 104 with FIG. 3 illustrating a 3D anatomical model. Additionally or alternatively, image data 410 may include a single plane or "slice" of the image data, as depicted in a thumbnail view 412 of graphical user interface 400. In some examples, image data 410 is graphically segmented to identify and indicate the location of anatomical features, such as an anatomic target, airways in the lungs, blood vessels, or the like.

Graphical user interface 400 displays information associated with planning a medical procedure in one or more views that are viewable to a user. Although illustrative arrangements of views are depicted in FIG. 3, it is to be understood that graphical user interface 400 may display any suitable number of views, in any suitable arrangement, and/or on any suitable number of screens. In some examples, the number of concurrently displayed views may be varied by opening and closing views, minimizing and maximizing views, moving views between a foreground and background of graphical user interface 400, switching between screens, and/or otherwise fully or partially obscuring views. Similarly, the arrangement of the views—including their size, shape, orientation, ordering (in a case of overlapping views), and/or the like—may vary and/or may be user-configurable.

At a process 220, a target location in the anatomical region is determined. For example, with reference to FIG. 3, a target location 416 for the target 106 may be determined in the anatomical region 104. In some examples, a user input for identifying the target location 416 in the three-dimensional anatomical region 104 is received via a user input device. In some embodiments, the user input may be provided by the user via a mouse, a touchscreen, a stylus, or the like. In some embodiments, the target location 416 may be determined without user input using, for example, image analysis techniques to determine target locations based on shape, density, location or other characteristics determined from computer analysis of the image data. As depicted in FIG. 3, the target location 416 may be displayed via graphical user interface 400. In this example, the target location 416 may correspond to a biopsy site. Also in this example, the target location 416 may represent a location of a target nodule.

As further illustrated in FIG. 3, in some examples, after the target location 416 is determined, a target border region 418 may be generated around the target location 416. The target border region 418 may be spherical, elliptical, rectangular, or any other shape. The target location 416 may represent a center C of the target border region 418 such that the target border region 418 expands outward from the target location 416. In examples when the anatomic target 106 represents a target nodule, a center of the target nodule may represent the center C of the target border region 418. In some examples, the target border region 418 is defined by a radius R. The radius R may be adjustable by a user, which will be described in further detail below.

At a process 230, and as illustrated in FIG. 3, an anatomical boundary is determined. For example, an anatomical boundary may indicate a portion of a surface in the three-dimensional anatomical region 104 such as a surface that is vulnerable, or otherwise of interest, and should be avoided (e.g., not touched, crossed, and/or punctured) by a medical instrument during the medical procedure. In some examples, the surface of interest in the anatomical region 104 may be a surface of pulmonary pleurae (e.g., pleurae 110), pulmonary fissures (e.g., fissure 112), large bullae, and/or blood vessels. In some examples, a graphical representation of an anatomical boundary 420 may be displayed via the graphical user interface 400. According to some examples, a graphical representation of the anatomical boundary 420 may be overlaid on the image data 410. As depicted in FIG. 3, a three-dimensional representation of the anatomical boundary 420 may be displayed as a translucent or grid-wire mesh on the three-dimensional anatomical model. A mesh may include a plurality of vertices. Additionally, in the thumbnail view 412, a cross sectional representation of the anatomical boundary 420 may be displayed as a curve overlaid on a CT slice. The graphical user interface 400 may also include an adjustment menu 430 that allows a user to adjust factors used to determine the anatomical boundary 420 or other graphically illustrated risk areas.

Figure 2B:
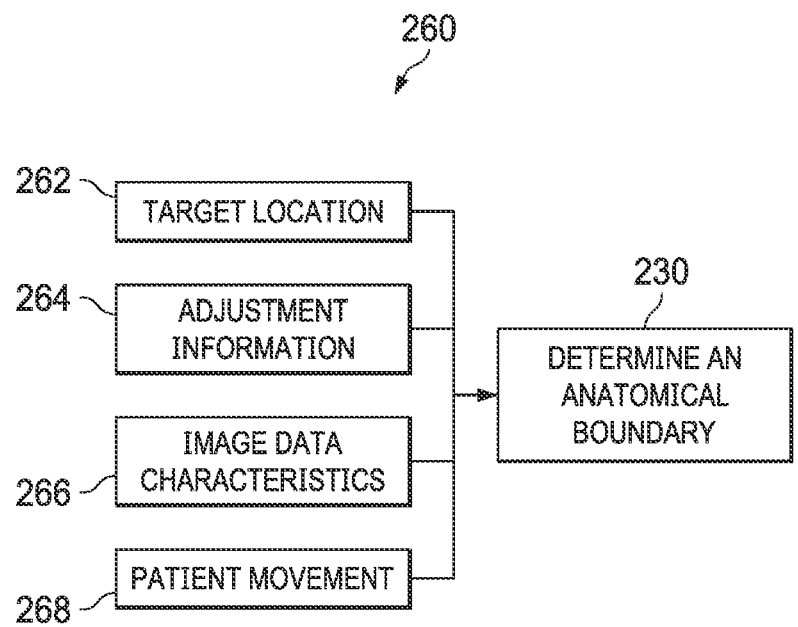
FIG. 2B is a diagram illustrating inputs for determining an anatomical boundary according to some examples.

FIG. 2B illustrates several inputs 262-268 that may be used to determine the anatomical boundary 420 at process 230 of method 200. Any of the inputs 262-268 may be omitted in determining the anatomical boundary 420, and other inputs may be used. As previously described, a target location input 262 may influence the determination of the anatomical boundary 420. For example, the location, shape, and size of the anatomical boundary 420 may be influenced by the location, shape, and size of the target location 416.

An adjustment information input 264 may also or alternatively influence the determination of the anatomical boundary 420. For example, the target border region 418 may intersect a surface of interest in the anatomical region to determine the anatomical boundary 420. The anatomical boundary 420 may represent the area of intersection between the target border region 418 and the surface of interest. The size of an area of intersection may vary depending on the length of the radius R of the target border region 418. For example, the area of intersection may increase as the length of the radius R increases. Accordingly, in some examples, the anatomical boundary 420 shown in the image data 410 may increase in size as the length of the radius R of the target border region 418 increases. As further illustrated in FIG. 3, the graphical user interface 400 may include an adjustment menu 430, which allows a user to adjust a size of the target border region 418. For example, the adjustment menu 430 may include an adjustment mechanism, such as a slider bar 432. The slider bar 432 illustrates a range of sizes for the target border region 418, ranging from a smallest size 434 to a largest size 436. The size of the target border region 418 may be based on the length of the radius R of the target border region 418. Thus, the smallest size 434 of the target border region 418 corresponds to a shortest length of the radius R. Similarly, the largest size 436 of the target border region 418 corresponds to a longest length of the radius R. When the slider bar 432 is adjusted, the radius R of the target border region 418 may also be adjusted. In some examples, a default radius for the radius R is 40 mm. In other examples, the radius R may be larger or smaller. For example, the radius R may range from 0 mm to 40 mm or from 40 mm to 120 mm. In other examples, the radius R may be larger than 120 mm. In some examples, the slider bar 432 may be adjusted based on user input.

An image data characteristics input 266 may also or alternatively influence the determination of the anatomical boundary 420. For example, the anatomical boundary 420 may represent areas of image data 410 with a characteristic such as a high intensity gradient, as a high intensity gradient indicates the presence of a surface of interest (e.g., the pleura of the lungs, a fissure of the lungs, a blood vessel wall, etc.). Computer vision techniques, including machine learning algorithms, may be applied to image data 410 to identify image data characteristics associated with candidate anatomical boundaries. Consistent with such examples, anatomical boundary 420 may include or be a portion of a candidate anatomical boundary determined by such computer vision or machine learning techniques.

A patient movement input 268 may also or alternatively influence the determination of the anatomical boundary 420. During navigation, the patient anatomy and consequently the three-dimensional anatomical model may move or become deformed by, for example, forces from the medical instrument (e.g., medical instrument 100), lung expiration and inspiration, and/or beating of the heart. The deformation may be measured, for example by a shape sensor in the medical instrument, or predicted by simulation, and the deformation may be applied to the three-dimensional anatomical model. The anatomical boundary 420 may likewise be adjusted or deformed to correspond to actual or planned deformation of the three-dimensional anatomical model.

In some examples, after the anatomical boundary 420 is determined, the user (e.g., the surgeon) may enter a manual adjustment mode to make further adjustments to the anatomical boundary 420. In the manual adjustment mode, the surgeon may manually edit and/or fine-tune the anatomical boundary 420. In that regard, the user may adjust any portion of the anatomical boundary 420. For example, the user may smooth out one or more portions of the anatomical boundary 420, connect one or more portions of the anatomical boundary 420 that may be disconnected, expand one or more portions of the anatomical boundary 420, reduce one or more portions of the anatomical boundary 420, etc. In some examples, an icon (e.g., a button, a pop up window, etc.) may be presented in the graphical user interface 400 to allow the user to enter the manual adjustment mode. For example, an icon 460 may be presented in the adjustment menu 430 that says "MODIFY BORDER" or "MANUAL EDIT." In such examples, the user may enter the manual adjustment mode by clicking and/or pressing the icon 460.

In the manual adjustment mode, in some examples, the manual adjustments may be made to a three-dimensional anatomical boundary, such as the anatomical boundary 420 overlaid on the image data 410. The user may rotate the anatomical boundary 420 in the graphical user interface 400 to view the anatomical boundary 420 from all angles. This allows the user to determine if all desired adjustments are made to the anatomical boundary 420. To manipulate/modify the anatomical boundary 420, the user may click and drag a portion of the anatomical boundary 420, for example. Alternately or additionally, the user may modify the anatomical boundary 420 to fill in any portion that may be missing and/or to connect any portions that may be disconnected. These adjustments may be made via an additional button, slider bar, or other icon that may be presented in the adjustment menu 430. In some examples, the user may move at least a portion of the anatomical boundary 420 outward in a direction away from the target border region 418. In some examples, the user may move at least a portion of the anatomical boundary 420 inward in a direction toward the target border region 418. The user may select a discrete portion of the anatomical boundary 420 to move toward or away from the target border region 418. Alternately or additionally, the entire anatomical boundary 420 may be moved toward or away from the target border region 418. In some examples, the user may draw a modified anatomical boundary in freehand, in polyline form, in a series of plotted points, or the like.

In alternative examples, in the manual adjustment mode, the manual adjustments may be made to a two-dimensional anatomical boundary (e.g., the anatomical boundary 420 illustrated in the thumbnail view 412). In such examples, the graphical user interface 400 may present the view 412 in the main viewing window and may present the image data 410 in a thumbnail view. Two-dimensional adjustments may be made to the anatomical boundary 420 in one or more of the manners discussed above with respect to three-dimensional adjustments. For example, the user may click and drag a portion of the anatomical boundary 420, fill in any portion of the anatomical boundary 420 that may be missing, and/or connect any portions of the anatomical boundary 420 that may be disconnected. In some examples, the anatomical boundary 420 may be moved away from or toward the target border region 418, as discussed above. Additionally, the user may draw a modified anatomical boundary in freehand, in polyline form, in a series of plotted points, or the like.

Figure 4A:
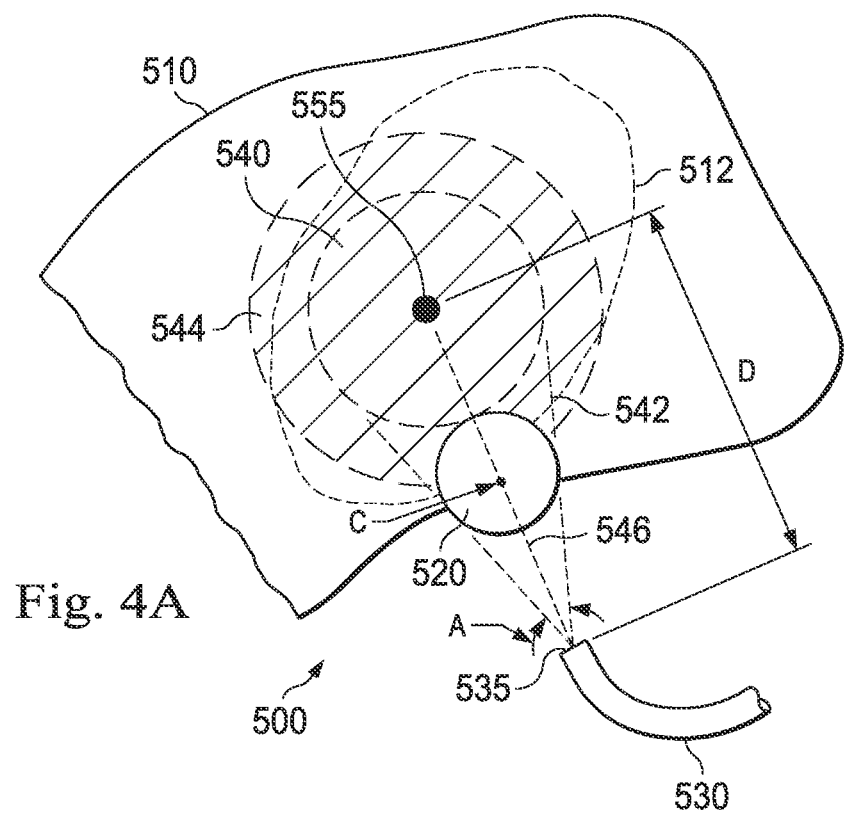
FIG. 4A is a simplified diagram illustrating guidance information associated with an anatomical boundary according to some examples.

Referring again to FIG. 2A, at a process 240, a trajectory zone may be determined around a path or tool trajectory between a medical instrument and the target location. For example, a trajectory zone may be determined around a path between the distal end 108 of the medical instrument 100 and the target 106. In another example, FIG. 4A illustrates a portion 500 of an anatomical region (e.g., anatomical region 104) near a target 520. A surface of interest 510 (e.g., surface of pleurae 110) extends near the target 520. An anatomical boundary 512 is determined on the surface of interest 510 as described at process 230. The medical procedure may be a biopsy procedure or any other type of medical procedure in which a medical instrument 530 (e.g., medical instrument 100) is inserted into the portion 500 of the anatomical region in the vicinity of the target 520. During the biopsy procedure, a biopsy tool, such as a biopsy needle, may extend from a distal end 535 (which may also be referred to as an exit point) of the medical instrument 530 towards the target 520. Accordingly, in the biopsy procedure, the anatomical boundary 512 may be behind the target 520 relative to distal end 535 and therefore may be at risk of being punctured if the needle, the instrument 530, or another instrument extending from distal end 535 extends too far past the target 520. A trajectory path 546 extends from the distal end 535 of medical instrument 530, through the target 520, to an intersection point 555 on the surface of interest 510. The trajectory path 546 may have a distance D. In some embodiments, the direction of the trajectory path 546 corresponds to an orientation of the distal end 535 of the medical instrument 530. In some embodiments, the trajectory path 546 extends through the center C of the target 520. A trajectory zone 542 extends around the trajectory path 546. The trajectory zone 542 may have a three-dimensional volume. As shown in FIG. 4A, the trajectory zone 542 is cone-shaped, but in other embodiments the trajectory zone 542 may be cylindrical, pyramidal, or any other suitable shape. In some embodiments, the trajectory zone 542 is symmetrical about the trajectory path 546 but in other embodiments may be off-center from the trajectory path 546. In some embodiments, uncertainty associated with the medical procedure (e.g., uncertainty in the location of exit point 535, uncertainty in the location of target 520, or both) may be factors in determining the trajectory zone 542.

In some examples, after the target border region 418 is generated, the target border region 418 is analyzed to determine whether at least a threshold percentage of the target border region 418 is located outside the surface of interest (which may be the pleura of the lungs, for example). In some examples, a default threshold percentage of the target border region 418 is 15%. In other examples, the threshold percentage of the target border region 418 may be larger or smaller. For example, the threshold percentage may range from 15%-30%. In other examples, the threshold percentage may be less than 15% or greater than 30%. In examples when the threshold percentage is not outside the surface of interest, the anatomical boundary 420 remains unchanged. In examples when the threshold percentage is outside the surface of interest, a determination is made regarding whether the target border region 418 is near a portion of interest (e.g., a blood vessel, the heart, etc.) that may indicate a sensitive anatomical region that raises concerns for potential unintentional damages during a procedure.

If the target border region 418 is not near a portion of interest, then the anatomical boundary 420 may be adjusted to encompass the portion of the target border region 418 that was determined to be outside the surface of interest. For example, a portion of the anatomical boundary 420 may be expanded so that all portions of the target border region 418 are included within the anatomical boundary 420. To expand the anatomical boundary, a first margin is generated. At least a portion of the first margin may illustrate the expanded portion of the anatomical boundary 420 and as such may be displayed in the graphical user interface 400. The center C of the target border region 418 may also be the center of the first margin. The first margin may expand radially outward from its center. Additionally, the first margin may be larger than the target border region 418. In other examples, the first margin may be the same size as the target border region 418.

In some examples, the first margin is sized based on the radius R of the target border region 418. For example, a radius of the first margin may be 5 mm greater than the radius R. In other examples, the radius of the first margin may be larger or smaller. For example, the radius of the first margin may be 3 mm greater than the radius R. In other examples, the radius of the first margin may be 6 mm greater than the radius R. The lengths discussed above for the radius of the first margin are discussed for exemplary purposes only—the radius of the first margin may be any other suitable length. After the first margin is generated, a second margin may be generated. The second margin may be larger than the first margin. As with the first margin, the center C of the target border region 418 may be the center of the second margin. The second margin may expand radially outward from its center. Additionally, the second margin may be sized based on the radius R of the target border region 418. For example, a radius of the second margin may be 25 mm greater than the radius R. In other examples, the radius of the second margin may be larger or smaller. For example, the radius of the second margin may be 20 mm greater than the radius R. In other examples, the radius of the second margin may be 30 mm greater than the radius R. The lengths discussed above for the radius of the second margin are discussed for exemplary purposes only—the radius of the second margin may be any other suitable length. After the second margin is determined, the control system may use the second margin to smooth out the first margin. This may be done to ensure that the anatomical boundary 420 smoothly transitions from the originally-determined anatomical boundary 420 to the expanded portion of the anatomical boundary 420 (i.e., the first margin) and back to the originally-determined anatomical boundary 420. A smooth anatomical boundary 420, including the first margin, may more closely represent the surface of interest by not depicting sharp corners or bends that may not be present in the surface of interest.

In other examples, if the target border region 418 is near a portion of interest, then a trajectory path (e.g., the trajectory path 546) may be determined. In some examples, the trajectory path may point away from or substantially away from the portion of interest. In such examples, the anatomical boundary 420 may be adjusted to encompass the portion of the target border region 418 that was determined to be outside the surface of interest, as discussed above. In other examples, the trajectory path may point toward or substantially toward the portion of interest. In such examples, the control system may disable (e.g., delete, hide, etc.) the determined anatomical boundary 420 and instead prompt the user to manually generate an anatomical boundary. Various systems and methods for manually generating an anatomical boundary are described in U.S. Provisional Patent Application No. 62/741,157 (filed on Oct. 4, 2018) (entitled "Graphical User Interface for Defining an Anatomical Boundary"), which is incorporated by reference herein in its entirety.

Figure 5:
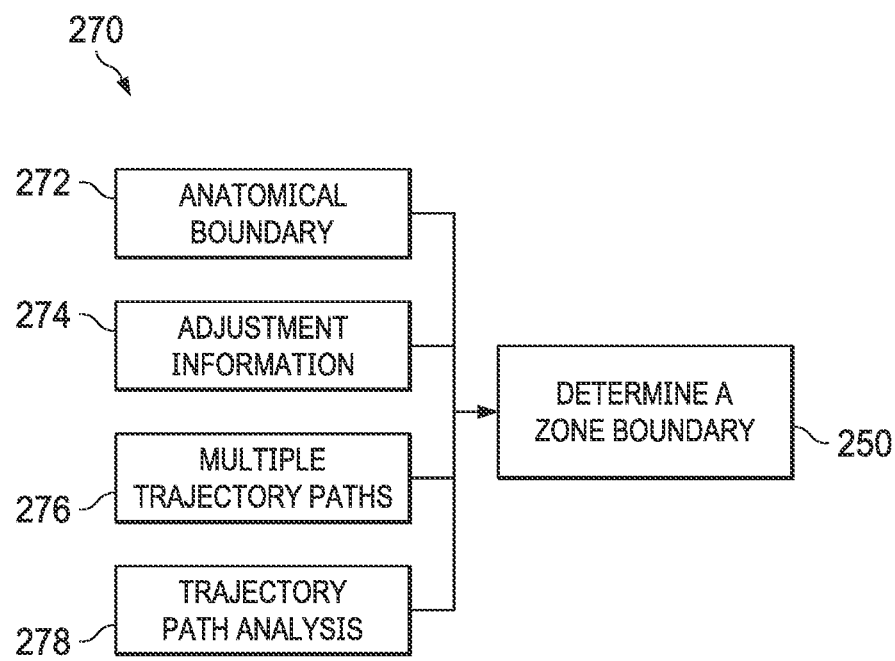
FIG. 5 is a diagram illustrating inputs for determining a zone boundary according to some examples.

At a process 250, a zone boundary may be determined based on one or more inputs as illustrated in FIG. 5. FIG. 5 illustrates several inputs 272-278 that may be used to determine the zone boundary. An anatomical boundary input 272 may influence the determination of the anatomical boundary (e.g., anatomical boundary 512). For example, the zone boundary may be determined based on an intersection of the trajectory zone 542 with the anatomical boundary 512. As shown in the example of FIG. 4A, a zone boundary 540 is determined based on an intersection of the anatomical boundary 512 and the trajectory zone 542. The zone boundary 540 may be a two- or three-dimensional area of the surface 510 that may be at risk of penetration by the biopsy instrument. In the example of FIG. 4A, the zone boundary 540 may extend entirely within the anatomical boundary 512 and thus have an area smaller than the anatomical boundary 512. In alternative examples, the zone boundary 540 be the same size and shape as the anatomical boundary 512. In other alternative examples, the zone boundary 540 may be the combination of the anatomical boundary 512 and the intersection of the trajectory zone 542 with the surface of interest 510. In some examples, the zone boundary 540 may include an additional margin 544 beyond the region directly within the trajectory zone 542. The additional margin 544 may be included to account for any uncertainty associated with the medical procedure (e.g., uncertainty in the location of exit point 535, uncertainty in the location of target 520, or both). In some examples, the zone boundary 540 may be determined in a binary manner (e.g., a given portion is either deemed at-risk or not) or in a gradual or continuous manner to reflect varying levels of risk at different locations.

An adjustment information input 274 may influence the determination of the zone boundary 540. In some examples, as shown in FIG. 3, the adjustment menu 430 may also include a slider bar 438. The slider bar 438 illustrates a range of angles for the trajectory zone 542 around the trajectory path 546 between the medical instrument 530 and the target location 520. In some examples, the slider bar 438 may be used to adjust an angle A of the trajectory zone 542. In some examples, a default angle A of the trajectory zone 542 is 120°. In other examples, the angle A of the trajectory zone 542 may be larger or smaller. For example, the angle A may range from 60° to 120° or from 120° to 180°. In other examples, the angle A may be less than 60° or greater than 180°. In some examples, a user input may control movement of the slider bar 438. In some examples, when the angle A of the trajectory zone 542 decreases, the size of the zone boundary 540 also decreases. In other examples, when the angle A of the trajectory zone 542 increases, the size of the zone boundary 540 also increases.

Figure 6:
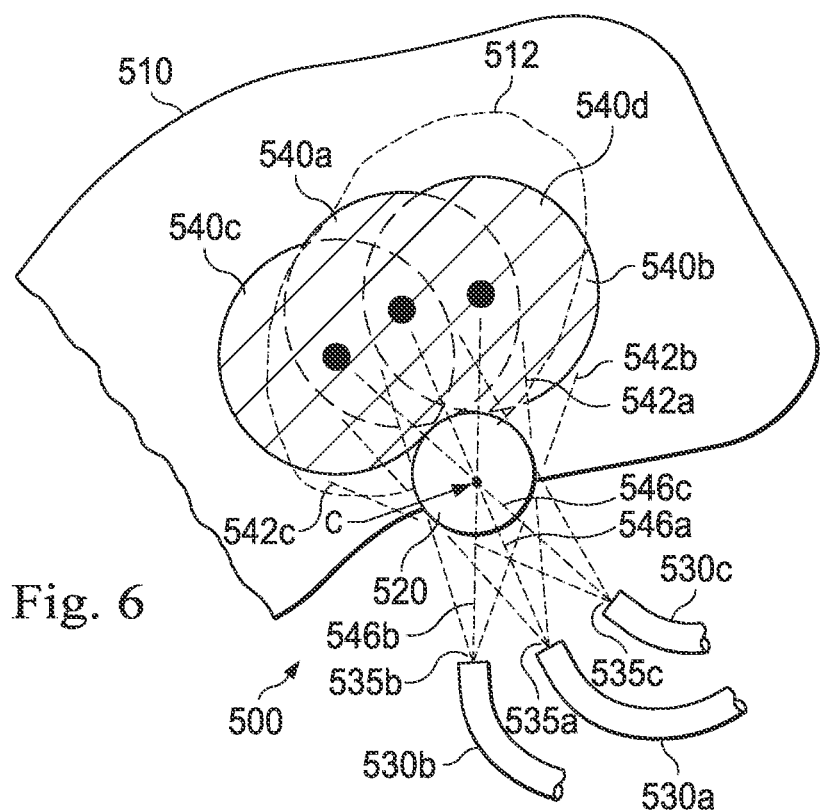
FIG. 6 is a simplified diagram illustrating guidance information associated with an anatomical boundary according to some examples.

A multiple trajectory path input 276 may also or alternatively influence the determination of the zone boundary 540. With reference to FIG. 6, in some cases, there may be more than one trajectory path available to the medical instrument 530 to reach the anatomic target 520. In such cases, the distal end 535 of the medical instrument 530 may be located in a different position and/or orientation within the patient anatomy depending on the chosen trajectory path. Each configuration of the distal end 535 may correspond to its own trajectory path, trajectory zone, and zone boundary. For example, with distal end 535*a* in the configuration as shown, a trajectory path 546*a* extends through the target 520, and a trajectory zone 542*a* around the trajectory path 546*a* generates a zone boundary 540*a* at the intersection of the anatomical surface 510. Likewise, with distal end 535*b* in the configuration as shown, a trajectory path 546*b* extends through the target 520, and a trajectory zone 542*b* around the trajectory path 546*b* generates a zone boundary 540*b* at the intersection of the anatomical surface 510. Likewise, with distal end 535*c* in the configuration as shown, a trajectory path 546*c* extends through the target 520, and a trajectory zone 542*c* around the trajectory path 546*c* generates a zone boundary 540*c* at the intersection of the anatomical surface 510. In such cases, a final or composite zone boundary 540*d* is determined based on the combined zone boundaries 540*a*, 540*b*, 540*c*, some of which may overlap each other. The zone boundary 540*d* may therefore indicate the at-risk portion of the surface 510 based on multiple trajectory paths of the instrument. The zone boundary 540d may be displayed as a single translucent or grid-wire mesh on the three-dimensional anatomical model. In other examples, the zone boundaries 540a, 540b, 540c may be displayed as multiple, separate translucent or grid-wire meshes on the three-dimensional anatomical model.

A trajectory path analysis input 278 may also or alternatively influence the determination of the zone boundary 540. In some embodiments, one or more trajectory paths (e.g., trajectory path 546) may be analyzed for viability to determine whether the distal end of the medical instrument is in an area of the patient anatomy that is separated from the target by a surface of interest. For example, a determination may be made as to whether the distal end of the medical instrument is in a different lobe of the patient lung, separated by a lung fissure, from the anatomic target. Because fissures of the patient anatomy separate the lobes of the patient anatomy, in situations when the instrument distal end and anatomic target are in different lobes, the biopsy needle would puncture a fissure when traveling along the trajectory path between the instrument distal end and the anatomic target. While this discussion makes reference to a fissure of the patient anatomy, it is to be understood that the discussion may also apply to any other portions of interest (e.g., large bullae, blood vessels, etc.). In some examples, an analysis may be conducted to determine whether a portion of the trajectory path 546 intersects with a portion of interest, such as a fissure. The fissure may be modeled as a mesh or a voxel mask generated based on the segmentation of image data. If the trajectory path 546 intersects the fissure model, a determination may be made that the trajectory path is unsafe and the trajectory path may be discarded, suppressed or otherwise not used in the determination of the zone boundary 540. In cases where a trajectory path does not intersect the fissure, a determination may be made that the trajectory path is acceptable and the trajectory path may be presented to a user as a candidate trajectory path.

Figure 4B:
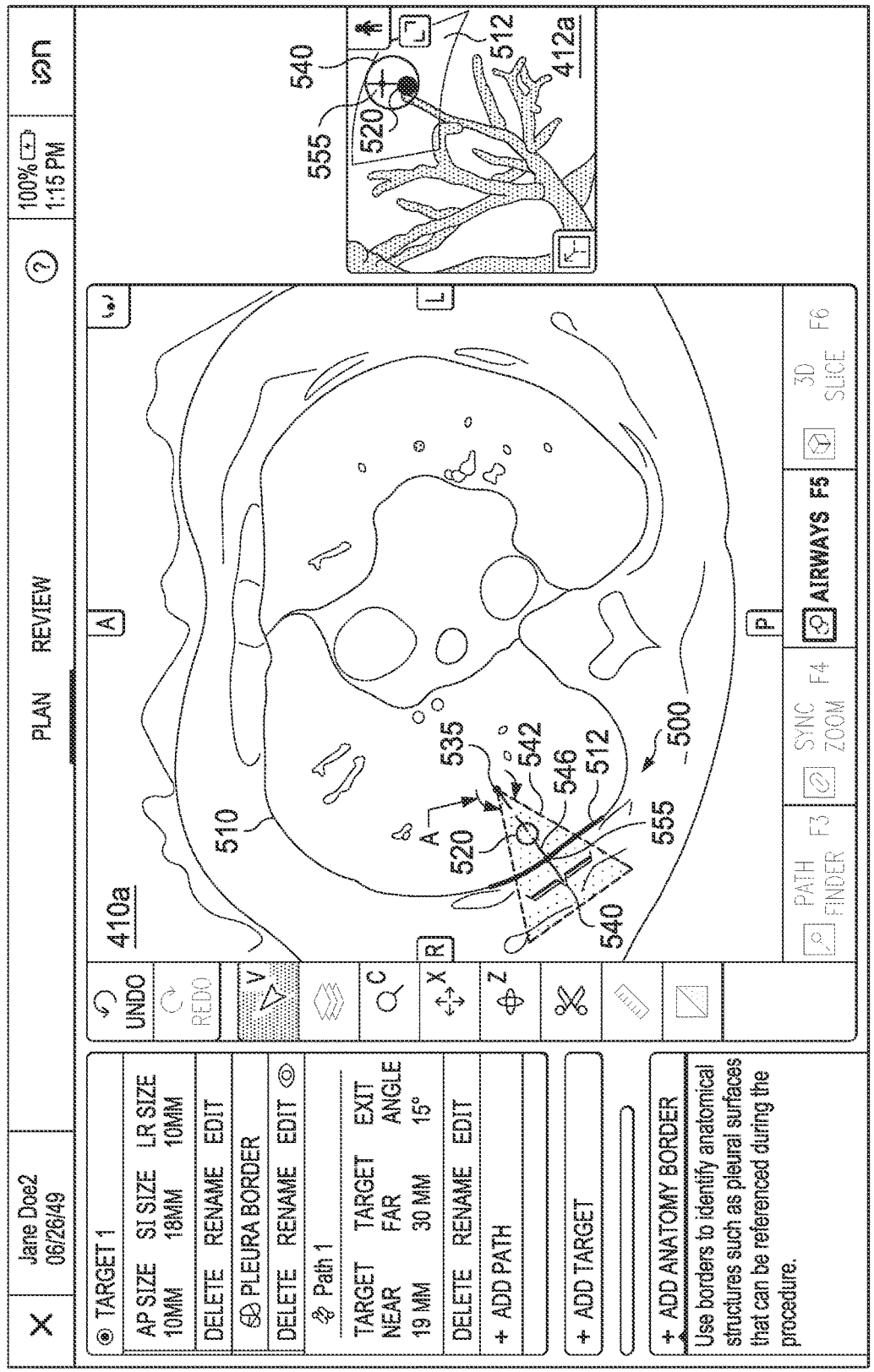
FIG. 4B is a simplified diagram of a graphical user interface that presents guidance information with two-dimensional image data according to some examples.

FIG. 4B illustrates the portion 500 of the anatomical region displayed on the graphical user interface 400 which provides guidance information during a planning mode. In the example of FIG. 4B, the guidance information may be depicted as a two-dimensional image, but in other embodiments may be depicted as a three-dimensional image. In this example, image data 410a is combined or overlayed with guidance information which may include graphical representations of the instrument distal end 535, the trajectory path 546, the trajectory zone 542, the intersection point 555, the anatomical boundary 512, and the zone boundary 540. Based on this guidance information, a user may be able to modify or fine tune the trajectory path 546, as needed. For example, the operator may adjust an orientation at which the distal end 535 of the medical instrument approaches the anatomic target 520. As another example, providing more space between the distal end 535 and the intersection point 555 may decrease the risk of the needle puncturing the surface 510 when the needle is extended. In some examples, pixels in the zone boundary 540 may be displayed in a different shade, color, or semi-transparent color overlay. Any of the guidance information graphics may be turned on or off, either automatically, by user selection, or by a combination. Additionally or alternatively, an indication of whether the anatomical boundary 512 fully encompasses the zone boundary 540 may be displayed or otherwise communicated to the operator. During the planning procedure, a safety score may be computed and provided to the operator that indicates the likelihood that the instrument and/or the tool will breach the anatomical boundary 512. Based on the score, the trajectory path 546 may be adjusted or revised to achieve a safer route. A variety of trajectory paths with different safety scores may be provided to the operator for selection.

Additionally or alternatively, image data 410a may include a single plane or "slice" of the image data, as depicted in a thumbnail view 412a of graphical user interface 400. In some examples, the thumbnail view 412a may also include the guidance information, as shown in FIG. 4B. The operator may use the guidance information in the image data 410a and in the thumbnail view 412a to modify or fine tune the trajectory path 546, as needed. In some cases, the guidance information is shown in the image data 410a but not in the thumbnail view 412a. In other cases, the guidance information is shown in the thumbnail view 412a but not in the image data 410a.

Figure 7A:
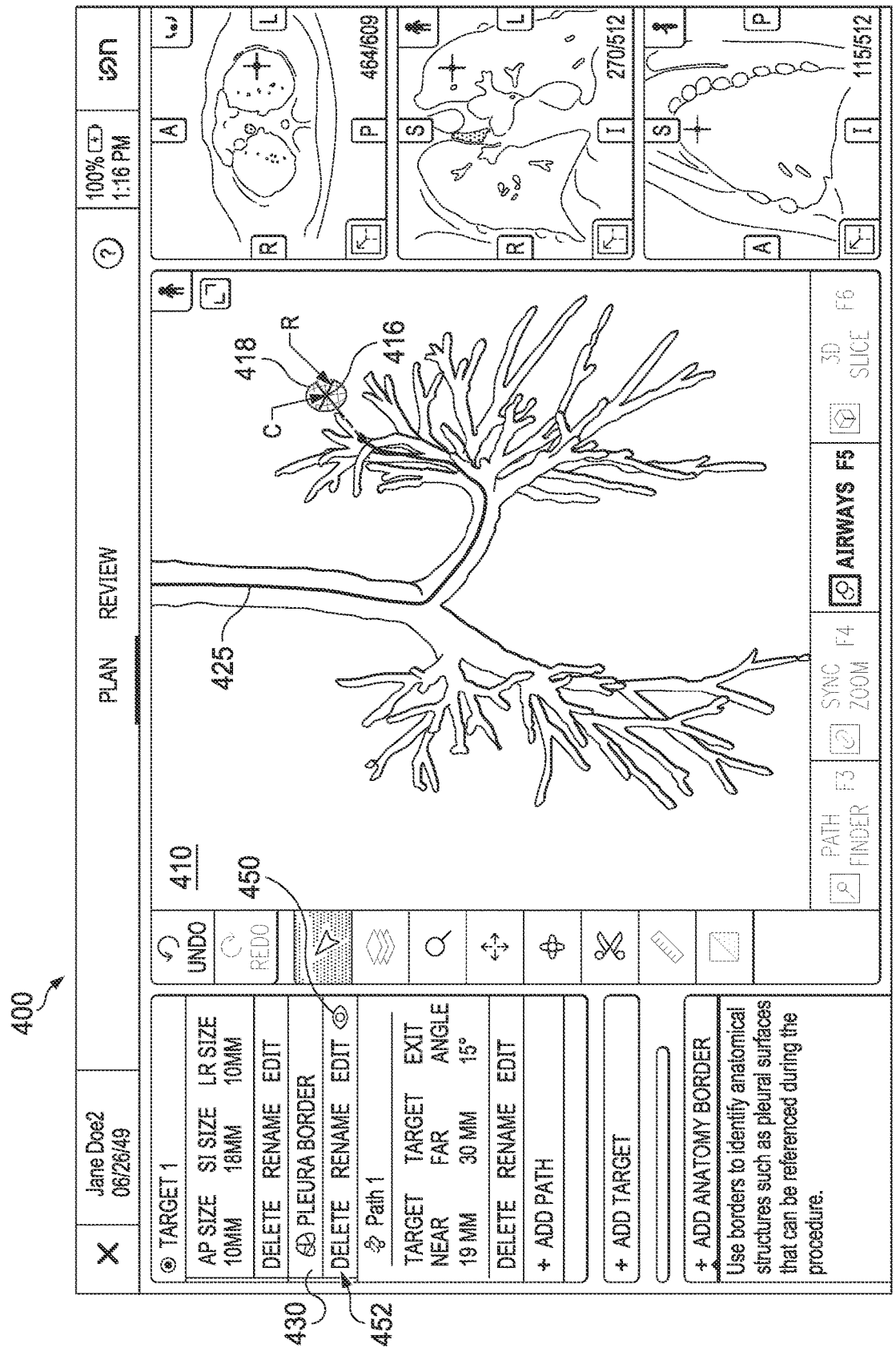
FIGS. 7A-7C are simplified diagrams of a graphical user interface during the performance of a method for generating an anatomical boundary according to some examples.

In some examples, one or more user inputs may be received to manipulate an anatomical boundary in a graphical user interface. FIG. 7A illustrates the graphical user interface 400 in the planning mode discussed above according to some examples. In the embodiment of FIG. 7A, the graphical user interface 400 includes a "show/hide" icon 450, which may be displayed, for example, in the adjustment menu 430. In some examples, the operator may want to more closely evaluate the portion of the three-dimensional anatomical model where the target location 416 is located. To achieve this evaluation, it may be beneficial to hide the anatomical boundary 420 in the image data 410. In some examples, when the anatomical boundary 420 is hidden, the data associated with the anatomical boundary 420 remains accessible in a control system—the anatomical boundary 420 is simply no longer displayed in the image data 410. As seen in FIG. 7A, the adjustment menu 430 includes the title "PLEURA BORDER," which indicates that an anatomical boundary 420 has been generated. The icon 450 allows the anatomical boundary 420 to be hidden and shown in the image data 410. For example, if the anatomical boundary 420 is displayed in the image data 410, the anatomical boundary 420 may be hidden based on user input. In some cases, the operator may select the icon 450 with a user input device. When the icon 450 is selected, the anatomical boundary 420 is hidden (i.e., temporarily not displayed) in the image data 410, as shown in FIG. 7A. To display the anatomical boundary 420 in the image data 410 again, a user input may be received selecting the icon 450. In several examples, the icon 450 may be selected to toggle the display of the anatomical boundary 420 on and off, as desired.

In some examples, when the anatomical boundary 420 is hidden, the distance D between the exit point 535 and the intersection point 555 may still be displayed. In other embodiments, when the anatomical boundary 420 is hidden, the distance D may also be hidden. Additionally or alternatively, when the anatomical boundary 420 is hidden, any other feature shown in the image data 410 (e.g., the target location 416, the target border region 418, the center C, the radius R, etc.) corresponding to the anatomical boundary 420 may also be hidden. In some examples, when the anatomical boundary 420 is hidden, the slider bars 432, 438 may be removed from the adjustment menu 430, as shown in FIG. 7A. When the anatomical boundary 420 is shown in the image data 410 again, the slider bars 432, 438 may also be shown in the adjustment menu 430 again. In other examples, when the anatomical boundary 420 is hidden, the slider bars 432, 438 may still be displayed in the adjustment menu 430.

Figure 7B:
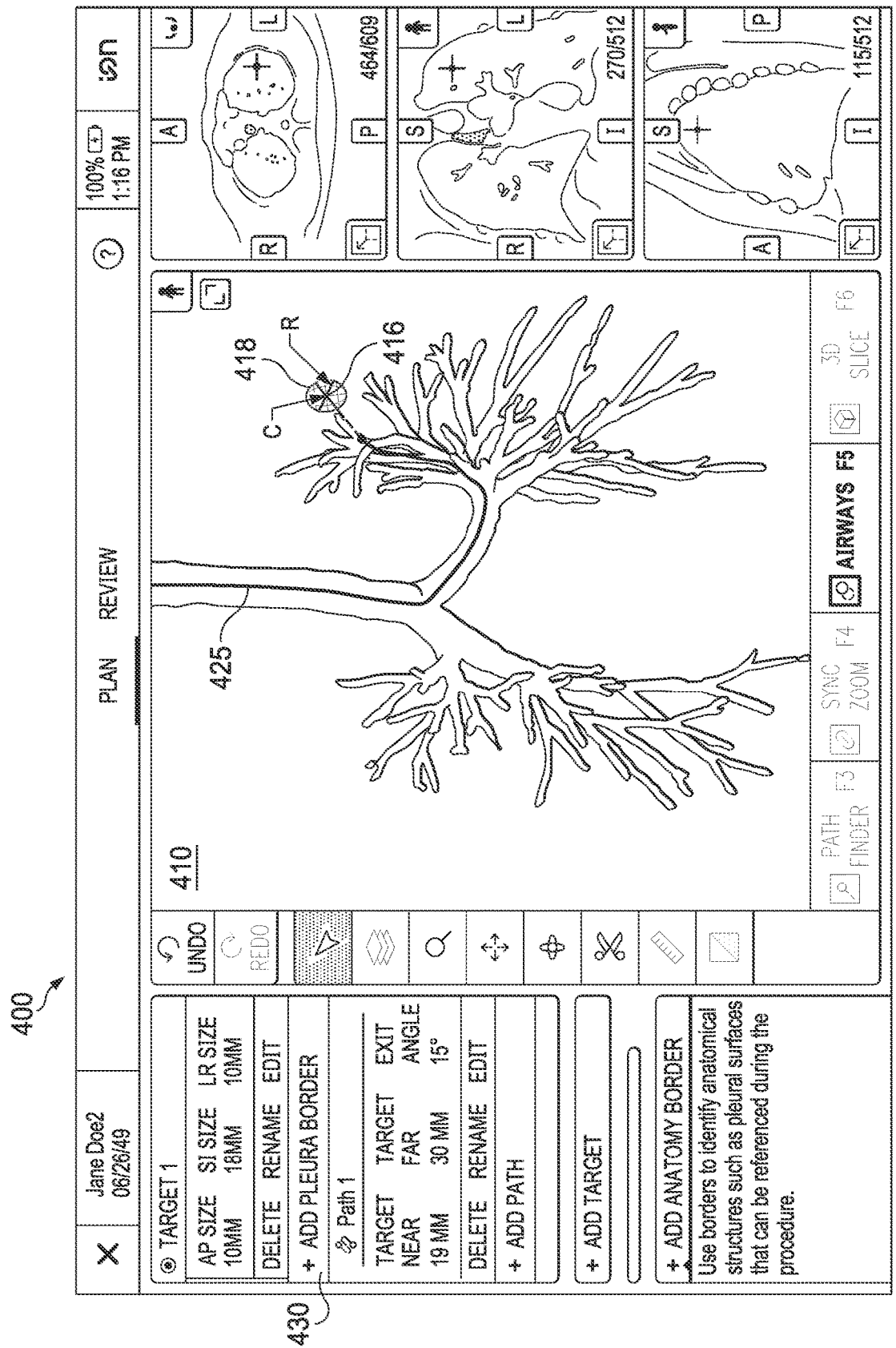

As shown in the embodiment of FIG. 7A, the graphical user interface 400 may also include a "delete" icon 452, which may be displayed, for example, in the adjustment menu 430. In some examples, the operator may want to have a new anatomical boundary generated, such as when a more accurate anatomical boundary may be obtained. In such examples, the current anatomical boundary 420 shown in the image data 410 may be deleted. In some examples, when the anatomical boundary 420 is deleted, the data associated with the anatomical boundary 420 is removed from the control system. For example, as seen in FIG. 7B, the adjustment menu 430 includes the title "ADD PLEURA BORDER," which indicates that an anatomical boundary has not been generated and/or has been deleted. The icon 452 allows the anatomical boundary 420 to be deleted from the image data 410. For example, if the anatomical boundary 420 is displayed in the image data 410, the anatomical boundary 420 may be deleted based on user input. In some cases, the operator may select the icon 452 with a user input device. When the icon 452 is selected, the anatomical boundary 420 is deleted from the image data 410, as shown in FIG. 7B, and may no longer be accessible in the control system. To display the anatomical boundary 420 in the image data 410 again, a new anatomical boundary 420 may be generated, as discussed above with respect to FIG. 2A.

In some examples, when the anatomical boundary 420 is deleted, the distance D between the exit point 535 and the intersection point 555 may also be deleted. Additionally, when the anatomical boundary 420 is deleted, any other feature shown in the image data 410 (e.g., the target location 416, the target border region 418, the center C, the radius R, etc.) corresponding to the anatomical boundary 420 may also be deleted.

Figure 7C:
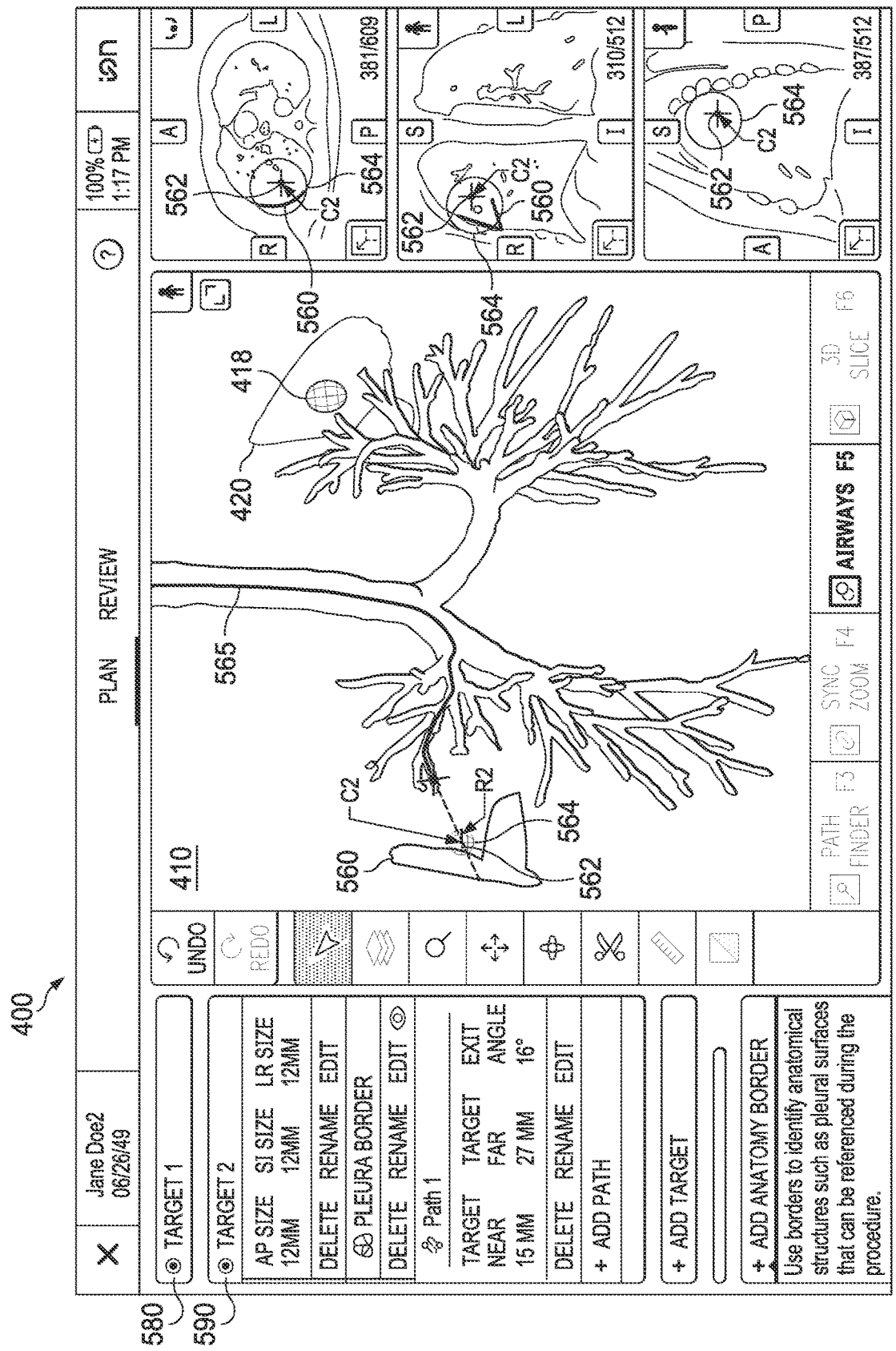

FIG. 7C illustrates the graphical user interface 400 in the planning mode discussed above according to some examples. In the embodiment of FIG. 7C, multiple anatomical boundaries 420, 560 are displayed via the graphical user interface 400. In some examples, more than one anatomic target may be present in the patient anatomy. In such examples, the operator may want to evaluate some or all of the anatomic targets. In such examples, it may be beneficial to have an anatomical boundary generated for some or all of the anatomic targets. Additionally, the graphical user interface 400 may include a menu corresponding to some or all of the anatomic targets. For example, as seen in FIG. 7C, the graphical user interface 400 includes a menu 580 labeled "TARGET 1" corresponding to the target location 516. As further shown in FIG. 7C, the graphical user interface 400 includes a menu 590 labeled "TARGET 2" corresponding to the target location 562. Each of the menus 580, 590 may include some or all of the features described above with respect to the graphical user interface 400 (e.g., an adjustment menu, a "show/hide" icon, a "delete" icon, etc.).

In some examples, when one of the menus 580, 590 is selected, the details corresponding to the selected menu may be displayed in the image data 410. For example, as shown in FIG. 7C, the menu 590 is selected. Because the menu 590 is selected, the details corresponding to the target location 562 are displayed in the image data 410. For example, the image data 410 may include the anatomical boundary 560, the target location 562, a target border region 564, a center C2 of the target border region 564, a radius R2 of the target border region 564, a traversal path 565, and/or any other details corresponding to the target location 562. In some examples, when the menu 590 is selected, the image data 410 may only display the details corresponding to the target location 562. In other examples, regardless of which menu 580, 590 is selected, some or all of the details corresponding to the target locations 562, 416 may be displayed in the image data 410. For example, as shown in FIG. 7C, the anatomical boundary 420 and the target border region 418 may also be displayed in the image data 410. In some embodiments, both menus 580, 590 may be selected at the same time, which may result in some or all of the details corresponding to the target locations being displayed in the image data 410. Additionally, as discussed above, one or more of the anatomical boundaries 420, 560 may be displayed as a translucent or grid-wire mesh on the three-dimensional anatomical model. Additionally or alternatively, to further distinguish between the anatomical boundaries 420, 560, the anatomical boundaries 420, 560 may be displayed in the image data 410 with different colors, patterns, etc.

The anatomical boundary 560 may be generated in the same manner as discussed above with respect to the generation of the anatomical boundary 420. Similarly, the target border region 564 may be generated and/or adjusted in the same manner as discussed above with respect to the target border region 418. In several examples, one or both of the anatomical boundaries 420, 560 may be displayed, hidden, or deleted, as discussed above. For example, if the operator wants to analyze the portion of the three-dimensional anatomic model surrounding the target location 562, the operator may choose to hide the anatomical boundary 420. Similarly, if the operator wants to analyze the portion of the three-dimensional anatomic model surrounding the target location 416, the operator may choose to hide the anatomical boundary 560. While FIG. 7C only illustrates two anatomical boundaries 420, 560, it is to be understood that any number of anatomical boundaries may be displayed corresponding to any number of anatomic targets. For example, three anatomical boundaries may be displayed corresponding to three anatomic targets, four anatomical boundaries may be displayed corresponding to four anatomic targets, etc.

As further shown in FIG. 7C, the menu 590 indicates that the anatomical boundary 560 is labeled "PLEURA BORDER." In some examples, the operator O may want to rename the anatomical boundary 560 to more easily determine which anatomical boundary is selected in examples when multiple anatomical boundaries are displayed. For example, the operator may input a different name for the anatomical boundary 560, such as "PLEURA BORDER 2," "FISSURE BORDER," "BLOOD VESSEL," or any other desired name. Additionally, the operator may rename the anatomical boundary 420 in the menu 580 to any desired name, such as "PLEURA BORDER 1," FISSURE BORDER," "BLOOD VESSEL," or any other desired name.

Figure 8:
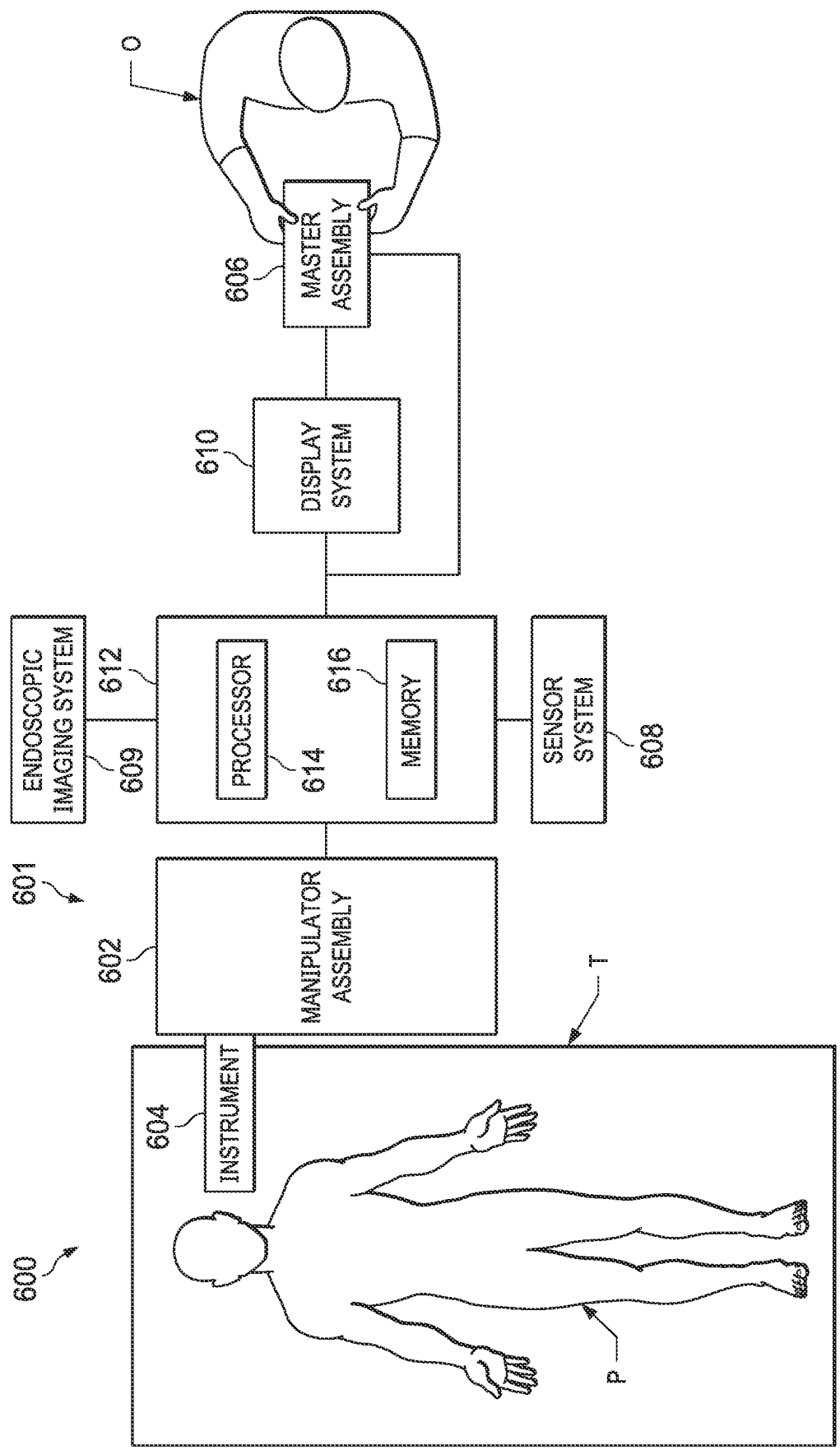
FIG. 8 is a simplified diagram of a medical system according to some examples.

In some embodiments, the planning techniques of this disclosure may be used in an image-guided medical procedure performed with a teleoperated medical system as described in further detail below. As shown in FIG. 8, a teleoperated medical system 600 generally includes a manipulator assembly 602 for operating a medical instrument 604 in performing various procedures on a patient P positioned on a table T in a surgical environment 601. The medical instrument 604 may correspond to the instrument 100. The manipulator assembly 602 may be teleoperated, non-teleoperated, or a hybrid teleoperated and non-teleoperated assembly with select degrees of freedom of motion that may be motorized and/or teleoperated and select degrees of freedom of motion that may be non-motorized and/or non-teleoperated. A master assembly 606, which may be inside or outside of the surgical environment 601, generally includes one or more control devices for controlling manipulator assembly 602. Manipulator assembly 602 supports medical instrument 604 and may optionally include a plurality of actuators or motors that drive inputs on medical instrument 604 in response to commands from a control system 612. The actuators may optionally include drive systems that when coupled to medical instrument 604 may advance medical instrument 604 into a naturally or surgically created anatomic orifice. Other drive systems may move the distal end of medical instrument 604 in multiple degrees of freedom, which may include three degrees of linear motion (e.g., linear motion along the X, Y, Z Cartesian axes) and in three degrees of rotational motion (e.g., rotation about the X, Y, Z Cartesian axes). Additionally, the actuators can be used to actuate an articulable end effector of medical instrument 604 for grasping tissue in the jaws of a biopsy device and/or the like.

Teleoperated medical system 600 also includes a display system 610 (which may include graphical user interface 400) for displaying an image or representation of the surgical site and medical instrument 604 generated by a sensor system 608 and/or an endoscopic imaging system 609. Display system 610 and master assembly 606 may be oriented so an operator O can control medical instrument 604 and master assembly 606 with the perception of telepresence. Any of the previously described graphical user interfaces may be displayable on a display system 610 and/or a display system of an independent planning workstation.

In some embodiments, medical instrument 604 may include components for use in surgery, biopsy, ablation, illumination, irrigation, or suction. Optionally medical instrument 604, together with sensor system 608 may be used to gather (e.g., measure or survey) a set of data points corresponding to locations within anatomic passageways of a patient, such as patient P. In some embodiments, medical instrument 604 may include components of the imaging system 609, which may include an imaging scope assembly or imaging instrument that records a concurrent or real-time image of a surgical site and provides the image to the operator or operator O through the display system 610. The concurrent image may be, for example, a two or three-dimensional image captured by an imaging instrument positioned within the surgical site. In some embodiments, the imaging system components that may be integrally or removably coupled to medical instrument 604. However, in some embodiments, a separate endoscope, attached to a separate manipulator assembly may be used with medical instrument 604 to image the surgical site. The imaging system 609 may be implemented as hardware, firmware, software or a combination thereof which interact with or are otherwise executed by one or more computer processors, which may include the processors of the control system 612.

The sensor system 608 may include a position/location sensor system (e.g., an electromagnetic (EM) sensor system) and/or a shape sensor system for determining the position, orientation, speed, velocity, pose, and/or shape of the medical instrument 604.

Teleoperated medical system 600 may also include control system 612. Control system 612 includes at least one memory 616 and at least one computer processor 614 for effecting control between medical instrument 604, master assembly 606, sensor system 608, endoscopic imaging system 609, and display system 610. Control system 612 also includes programmed instructions (e.g., a non-transitory machine-readable medium storing the instructions) to implement a plurality of operating modes of the teleoperational system including a navigation planning mode, a navigation mode, and/or a procedure mode. Control system 612 also includes programmed instructions (e.g., a non-transitory machine-readable medium storing the instructions) to implement some or all of the methods described in accordance with aspects disclosed herein, including, for example, instructions for providing information to display system 610, instructions for determining a target location, instructions for determining an anatomical boundary, instructions for determining a trajectory zone, instructions for determining a zone boundary, and instructions for receiving user (e.g., operator O) inputs to a planning mode.

A plan for a medical procedure, such as a biopsy procedure, may be saved and used by the control system 612 to provide automated navigation or operator navigation assistance of a medical instrument to perform the biopsy procedure. During navigation, the control system 612 may display an anatomical boundary and/or a zone boundary with a three-dimensional anatomic model of the anatomic region, with an endoluminal view, or with other anatomical views presented on a user display. The anatomical boundary and/or a zone boundary may also or alternatively be displayed with (e.g., overlaid on) registered images from other imaging technology such as fluoroscopic images obtained during a medical procedure.

Control system 612 may optionally further include a virtual visualization system to provide navigation assistance to operator O when controlling medical instrument 604 during an image-guided surgical procedure. Virtual navigation using the virtual visualization system may be based upon reference to an acquired pre-operative or intra-operative dataset of anatomic passageways. The virtual visualization system processes images of the surgical site imaged using imaging technology such as computerized tomography (CT), magnetic resonance imaging (MRI), fluoroscopy, thermography, ultrasound, optical coherence tomography (OCT), thermal imaging, impedance imaging, laser imaging, nanotube X-ray imaging, and/or the like.

Figure 9:
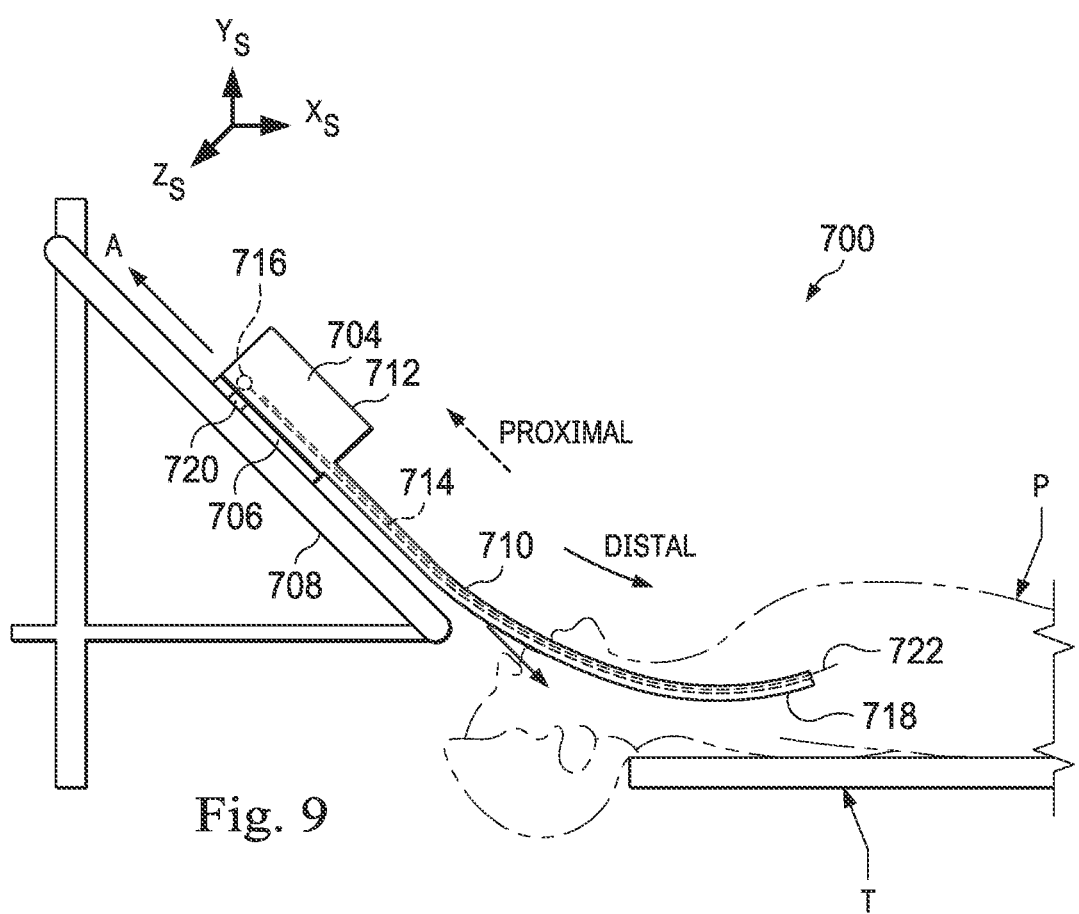
FIG. 9 is a simplified diagram of a side view of a patient coordinate space including a medical instrument mounted on an insertion assembly according to some examples.

FIG. 9 illustrates a surgical environment 700 in which the patient P is positioned on the table T. Patient P may be stationary within the surgical environment in the sense that gross patient movement is limited by sedation, restraint, and/or other means. Cyclic anatomic motion including respiration and cardiac motion of patient P may continue unless the patient is asked to hold his or her breath to temporarily suspend respiratory motion. Within surgical environment 700, a medical instrument 704 (e.g., the instrument 100, 604), having the instrument frame of reference ($X_S$, $Y_S$, $Z_S$), is coupled to an instrument carriage 706. In this embodiment, medical instrument 704 includes an elongate device 710, such as a flexible catheter, coupled to an instrument body 712. Instrument carriage 706 is mounted to an insertion stage 708 fixed within surgical environment 700. Alternatively, insertion stage 708 may be movable but have a known location (e.g., via a tracking sensor or other tracking device) within surgical environment 700. In these alternatives, the medical instrument frame of reference is fixed or otherwise known relative to the surgical frame of reference. Instrument carriage 706 may be a component of a teleoperational manipulator assembly (e.g., teleoperational manipulator assembly 602) that couples to medical instrument 704 to control insertion motion (i.e., motion along an axis A) and, optionally, motion of a distal end 718 of the elongate device 710 in multiple directions including yaw, pitch, and roll. Instrument carriage 706 or insertion stage 708 may include actuators, such as servomotors, (not shown) that control motion of instrument carriage 706 along insertion stage 708.

In this embodiment, a sensor system (e.g., sensor system 608) includes a shape sensor 714. Shape sensor 714 may include an optical fiber extending within and aligned with elongate device 710. In one embodiment, the optical fiber has a diameter of approximately 200 μm. In other embodiments, the dimensions may be larger or smaller. The optical fiber of shape sensor 714 forms a fiber optic bend sensor for determining the shape of the elongate device 710. In one alternative, optical fibers including Fiber Bragg Gratings (FBGs) are used to provide strain measurements in structures in one or more dimensions. Various systems and methods for monitoring the shape and relative position of an optical fiber in three dimensions are described in U.S. patent application Ser. No. 11/180,389 (filed Jul. 13, 2005) (disclosing "Fiber optic position and shape sensing device and method relating thereto"); U.S. patent application Ser. No. 12/047,056 (filed on Jul. 16, 2004) (disclosing "Fiber-optic shape and relative position sensing"); and U.S. Pat. No. 6,389,187 (filed on Jun. 17, 1998) (disclosing "Optical Fibre Bend Sensor"), which are all incorporated by reference herein in their entireties. Sensors in some embodiments may employ other suitable strain sensing techniques, such as Rayleigh scattering, Raman scattering, Brillouin scattering, and Fluorescence scattering. In some embodiments, the shape of the catheter may be determined using other techniques. For example, a history of the distal end pose of elongate device 710 can be used to reconstruct the shape of elongate device 710 over the interval of time.

As shown in FIG. 9, instrument body 712 is coupled and fixed relative to instrument carriage 706. In some embodiments, the optical fiber shape sensor 714 is fixed at a proximal point 716 on instrument body 712. In some embodiments, proximal point 716 of optical fiber shape sensor 714 may be movable along with instrument body 712 but the location of proximal point 716 may be known (e.g., via a tracking sensor or other tracking device). Shape sensor 714 measures a shape from proximal point 716 to another point such as distal end 718 of elongate device 710.

Elongate device 710 includes a channel (not shown) sized and shaped to receive a medical instrument 722. In some embodiments, medical instrument 722 may be used for procedures such as surgery, biopsy, ablation, illumination, irrigation, or suction. Medical instrument 722 can be deployed through elongate device 710 and used at a target location within the anatomy. Medical instrument 722 may include, for example, image capture probes, biopsy instruments, laser ablation fibers, and/or other surgical, diagnostic, or therapeutic tools. Medical instrument 722 may be advanced from the distal end 718 of the elongate device 710 to perform the procedure and then retracted back into the channel when the procedure is complete. Medical instrument 722 may be removed from proximal end of elongate device 710 or from another optional instrument port (not shown) along elongate device 710.

Elongate device 710 may also house cables, linkages, or other steering controls (not shown) to controllably bend distal end 718. In some examples, at least four cables are used to provide independent "up-down" steering to control a pitch of distal end 718 and "left-right" steering to control a yaw of distal end 718.

A position measuring device 720 may provide information about the position of instrument body 712 as it moves on insertion stage 708 along an insertion axis A. Position measuring device 720 may include resolvers, encoders, potentiometers, and/or other sensors that determine the rotation and/or orientation of the actuators controlling the motion of instrument carriage 706 and consequently the motion of instrument body 712. In some embodiments, insertion stage 708 is linear, while in other embodiments, the insertion stage 708 may be curved or have a combination of curved and linear sections.

In the description, specific details have been set forth describing some embodiments. Numerous specific details are set forth in order to provide a thorough understanding of the embodiments. It will be apparent, however, to one skilled in the art that some embodiments may be practiced without some or all of these specific details. The specific embodiments disclosed herein are meant to be illustrative but not limiting. One skilled in the art may realize other elements that, although not specifically described here, are within the scope and the spirit of this disclosure.

Elements described in detail with reference to one embodiment, implementation, or application optionally may be included, whenever practical, in other embodiments, implementations, or applications in which they are not specifically shown or described. For example, if an element is described in detail with reference to one embodiment and is not described with reference to a second embodiment, the element may nevertheless be claimed as included in the second embodiment. Thus, to avoid unnecessary repetition in the following description, one or more elements shown and described in association with one embodiment, implementation, or application may be incorporated into other embodiments, implementations, or aspects unless specifically described otherwise, unless the one or more elements would make an embodiment or implementation non-functional, or unless two or more of the elements provide conflicting functions. Not all the illustrated processes may be performed in all embodiments of the disclosed methods. Additionally, one or more processes that are not expressly illustrated in may be included before, after, in between, or as part of the illustrated processes. In some embodiments, one or more of the processes may be performed by a control system or may be implemented, at least in part, in the form of executable code stored on non-transitory, tangible, machine-readable media that when run by one or more processors may cause the one or more processors to perform one or more of the processes.

Any alterations and further modifications to the described devices, instruments, methods, and any further application of the principles of the present disclosure are fully contemplated as would normally occur to one skilled in the art to which the disclosure relates. In addition, dimensions provided herein are for specific examples and it is contemplated that different sizes, dimensions, and/or ratios may be utilized to implement the concepts of the present disclosure. To avoid needless descriptive repetition, one or more components or actions described in accordance with one illustrative embodiment can be used or omitted as applicable from other illustrative embodiments. For the sake of brevity, the numerous iterations of these combinations will not be described separately. For simplicity, in some instances the same reference numbers are used throughout the drawings to refer to the same or like parts.

The systems and methods described herein may be suited for navigation and treatment of anatomic tissues, via natural or surgically created connected passageways, in any of a variety of anatomic systems, including the lung, colon, the intestines, the kidneys and kidney calices, the brain, the heart, the circulatory system including vasculature, and/or the like. While some embodiments are provided herein with respect to medical procedures, any reference to medical or surgical instruments and medical or surgical methods is non-limiting. For example, the instruments, systems, and methods described herein may be used for non-medical purposes including industrial uses, general robotic uses, and sensing or manipulating non-tissue work pieces. Other example applications involve cosmetic improvements, imaging of human or animal anatomy, gathering data from human or animal anatomy, and training medical or non-medical personnel. Additional example applications include use for procedures on tissue removed from human or animal anatomies (without return to a human or animal anatomy) and performing procedures on human or animal cadavers. Further, these techniques can also be used for surgical and nonsurgical medical treatment or diagnosis procedures.

One or more elements in embodiments of this disclosure may be implemented in software to execute on a processor of a computer system such as control processing system. When implemented in software, the elements of the embodiments of this disclosure may be code segments to perform various tasks. The program or code segments can be stored in a processor readable storage medium or device that may have been downloaded by way of a computer data signal embodied in a carrier wave over a transmission medium or a communication link. The processor readable storage device may include any medium that can store information including an optical medium, semiconductor medium, and/or magnetic medium. Processor readable storage device examples include an electronic circuit; a semiconductor device, a semiconductor memory device, a read only memory (ROM), a flash memory, an erasable programmable read only memory (EPROM); a floppy diskette, a CD-ROM, an optical disk, a hard disk, or other storage device. The code segments may be downloaded via computer networks such as the Internet, Intranet, etc. Any of a wide variety of centralized or distributed data processing architectures may be employed. Programmed instructions may be implemented as a number of separate programs or subroutines, or they may be integrated into a number of other aspects of the systems described herein. In some examples, the control system may support wireless communication protocols such as Bluetooth, Infrared Data Association (IrDA), HomeRF, IEEE 802.11, Digital Enhanced Cordless Telecommunications (DECT), ultra-wideband (UWB), ZigBee, and Wireless Telemetry.

Note that the processes and displays presented may not inherently be related to any particular computer or other apparatus. Various general-purpose systems may be used with programs in accordance with the teachings herein, or it may prove convenient to construct a more specialized apparatus to perform the operations described. The required structure for a variety of these systems will appear as elements in the claims. In addition, the embodiments of the invention are not described with reference to any particular programming language. It will be appreciated that a variety of programming languages may be used to implement the teachings of the invention as described herein.

This disclosure describes various instruments, portions of instruments, and anatomic structures in terms of their state in three-dimensional space. As used herein, the term "position" refers to the location of an object or a portion of an object in a three-dimensional space (e.g., three degrees of translational freedom along Cartesian x-, y-, and z-coordinates). As used herein, the term "orientation" refers to the rotational placement of an object or a portion of an object (three degrees of rotational freedom—e.g., roll, pitch, and yaw). As used herein, the term "pose" refers to the position of an object or a portion of an object in at least one degree of translational freedom and to the orientation of that object or portion of the object in at least one degree of rotational freedom (up to six total degrees of freedom). As used herein, the term "shape" refers to a set of poses, positions, or orientations measured along an object.

While certain exemplary embodiments of the invention have been described and shown in the accompanying drawings, it is to be understood that such embodiments are merely illustrative of and not restrictive on the broad invention, and that the embodiments of the invention not be limited to the specific constructions and arrangements shown and described, since various other modifications may occur to those ordinarily skilled in the art.

Various aspects of the subject matter described herein are set forth in the following numbered examples.

Example 1: A medical system comprising: a display system; a user input device; a medical instrument; and a control system communicatively coupled to the display system and the user input device, the control system configured to: display image data of an anatomical region via the display system; determine a target location in the anatomical region; determine an anatomical boundary based on the target location, the anatomical boundary indicating a surface of an anatomical structure in the anatomical region; determine a trajectory zone around a path between the medical instrument and the target location; and determine a zone boundary based on an intersection of the trajectory zone with the anatomical boundary.

Example 2: The medical system of example 1, wherein the zone boundary is displayed in overlay on the image data via the display system.

Example 3: The medical system of example 1, wherein determining the anatomical boundary comprises determining a target border region around the target location.

Example 4: The medical system of example 1, wherein the control system is further configured to display a tool trajectory of a tool, the tool extendable from the medical instrument along the path.

Example 5: The medical system of example 1, wherein determining the trajectory zone comprises determining a plurality of trajectory zones, the plurality of trajectory zones including the trajectory zone.

Example 6: The medical system of example 1, wherein the zone boundary corresponds to a three-dimensional surface mesh that includes a plurality of vertices.

Example 7: The medical system of example 1, wherein the control system is further configured to display the zone boundary overlaid on an anatomic model derived from the image data via the display system.

Example 8: The medical system of example 1, wherein the control system is further configured to determine a viability of the path.

Example 9: A method of planning a medical procedure, the method comprising: displaying image data of an anatomical region via a display system; determining a target location in the anatomical region; determining an anatomical boundary based on the target location, the anatomical boundary indicating a surface of an anatomical structure in the anatomical region; determining a trajectory zone around a path between a medical instrument and the target location; and determining a zone boundary based on an intersection of the trajectory zone with the anatomical boundary.

Example 10: The method of example 9, further comprising displaying the zone boundary with the image data via the display system.

Example 11: The method of example 9, wherein displaying the zone boundary comprises displaying the zone boundary in overlay on the image data via the display system.

Example 12: The method of example 9, wherein determining the anatomical boundary comprises determining a target border region around the target location.

Example 13: The method of example 12, wherein determining the anatomical boundary further comprises determining at least one intersection of the target border region with the anatomical structure.

Example 14: The method of example 9, wherein determining the trajectory zone comprises determining a distance between a distal end of the medical instrument and a distal end of a tool extendable from the medical instrument along the path.

Example 15: The method of example 14, further comprising displaying a tool trajectory of the tool.

Example 16: The method of example 15, further comprising displaying an intersection point between the tool trajectory and the zone boundary.

Example 17: The method of example 9, wherein the trajectory zone is cone-shaped.

Example 18: The method of example 17, further comprising receiving a user input adjusting an angle of the cone-shaped trajectory zone.

Example 19: The method of example 9, wherein determining the trajectory zone comprises determining a plurality of trajectory zones, the plurality of trajectory zones including the trajectory zone.

Example 20: The method of example 19, wherein determining the zone boundary comprises determining the zone boundary based on an intersection of each trajectory zone of the plurality of trajectory zones with the anatomical boundary.

Example 21: The method of example 9, wherein the zone boundary corresponds to a three-dimensional surface mesh that includes a plurality of vertices.

Example 22: The method of example 9, further comprising displaying, via the display system, guidance information during the determination of the zone boundary.

Example 23: The method of example 9, further comprising displaying, via the display system, the zone boundary overlaid on an anatomic model derived from the image data.

Example 24: The method of example 23, further comprising deforming the zone boundary to conform with deformations of the anatomic model based on movement of a patient anatomy.

Example 25: The method of example 9, further comprising displaying the anatomical boundary overlaid on fluoroscopic image data obtained during a patient procedure.

Example 26: The method of example 9, further comprising: receiving a user input while the medical instrument is located within the anatomical region; and responsive to the user input, directing an orientation of a distal end of the medical instrument away from the zone boundary.

Example 27: The method of example 9, further comprising determining a distance between a distal end of a virtual medical instrument and the zone boundary.

Example 28: The method of example 9, further comprising determining a distance between a distal end of a tool and the zone boundary, the tool being extendable from the medical instrument along the path.

Example 29: The method of example 28, further comprising providing a visual, audible, or haptic indicator when the distance between the distal end of the tool and the zone boundary is less than a predetermined threshold distance.

Example 30: The method of example 28, further comprising altering an advancement speed of the tool based on the determined distance.

Example 31: The method of example 9, further comprising providing one or more suggested deployment locations for the medical instrument, wherein the one or more suggested deployment locations are located at least a threshold distance from the zone boundary.

Example 32: The method of example 9, further comprising determining a viability of the path.

Example 33: The method of example 32, wherein determining the viability of the path comprises determining whether a tool extendable from the medical instrument will puncture a portion of interest of a patient anatomy along the path.

Example 34: The method of example 33, wherein the portion of interest includes at least one of a pleura of the patient anatomy, a fissure of the patient anatomy, or blood vessels in the patient anatomy.

What is claimed is:

1. A medical system comprising:
   a display system; and
   a control system communicatively coupled to the display system, the control system configured to:
   display image data of an anatomical region via the display system;
   determine a target location in the anatomical region;
   determine an anatomical boundary based on the target location, the anatomical boundary indicating a surface of an anatomical structure in the anatomical region, the anatomical structure to be avoided by a tool extendable from a medical instrument;
   determine a trajectory zone around a path between a distal end of the medical instrument and the target location, wherein the target location is between the distal end of the medical instrument and the anatomical boundary; and
   determine a zone boundary based on an intersection of the trajectory zone with the anatomical boundary.

2. The medical system of claim 1, wherein the control system is further configured to display the zone boundary with the image data via the display system.

3. The medical system of claim 1, wherein determining the anatomical boundary further comprises determining at least one intersection of a target border region with the anatomical structure.

4. The medical system of claim 1, wherein determining the trajectory zone comprises determining a distance between the distal end of the medical instrument and a distal end of the tool extendable from the medical instrument.

5. The medical system of claim 4, wherein the control system is further configured to display an intersection point between the zone boundary and a tool trajectory of the tool.

6. The medical system of claim 4, wherein the tool includes a needle.

7. The medical system of claim 1, wherein the trajectory zone is cone-shaped.

8. The medical system of claim 7, wherein an angle of the cone-shaped trajectory zone is adjustable.

9. The medical system of claim 1, wherein determining the zone boundary comprises determining additional trajectory zones and determining the zone boundary based on an intersection of each trajectory zone with the anatomical boundary.

10. The medical system of claim 1, wherein the control system is further configured to display guidance information via the display system during the determination of the zone boundary.

11. The medical system of claim 1, wherein the control system is further configured to deform the zone boundary to conform with deformations of an anatomic model derived from the image data based on movement of a patient anatomy and display the deformed zone boundary.

12. The medical system of claim 1, wherein the control system is further configured to display the anatomical boundary overlaid on fluoroscopic image data obtained during a patient procedure.

13. The medical system of claim 1, wherein the control system is further configured to:
receive a user input via a user input device while the medical instrument is located within the anatomical region; and
responsive to the user input, direct an orientation of the distal end of the medical instrument away from the zone boundary.

14. The medical system of claim 1, wherein the control system is further configured to determine a distance between a distal end of the tool and the zone boundary.

15. The medical system of claim 14, wherein the control system is further configured to provide a visual, audible, or haptic indicator when the distance between the distal end of the tool and the zone boundary is less than a predetermined threshold distance.

16. The medical system of claim 14, wherein the control system is further configured to alter an advancement speed of the tool based on the determined distance.

17. The medical system of claim 1, wherein the control system is further configured to provide one or more suggested deployment locations for the medical instrument, wherein the one or more suggested deployment locations are located at least a threshold distance from the zone boundary.

18. The medical system of claim 1, wherein the control system is further configured to determine a viability of the path including determining whether the tool extendable from the medical instrument will puncture a portion of interest of a patient anatomy along the path.

19. The medical system of claim 18, wherein the portion of interest includes at least one of a pleura of the patient anatomy, a fissure of the patient anatomy, or blood vessels in the patient anatomy.

20. The medical system of claim 1, wherein the control system is further configured to display the target location with the image data via the display system.

* * * * *